United States Patent [19]
Montner

[11] Patent Number: 5,618,848
[45] Date of Patent: Apr. 8, 1997

[54] BETA-AGONISTS AS AN AID TO MAINTAIN OR ENHANCE STRENGTH AND ENDURANCE

[75] Inventor: Paul Montner, Albuquerque, N.M.

[73] Assignee: University of New Mexico, Albuquerque, N.M.

[21] Appl. No.: 435,974

[22] Filed: May 5, 1995

[51] Int. Cl.$^6$ .................................................. A61K 31/135
[52] U.S. Cl. ............................................ 514/653; 514/651
[58] Field of Search ...................................... 514/653, 651

[56] References Cited

PUBLICATIONS

"Prevention of Bedrest–induced Physical Deconditioning by Daily Dobutamine Infusions"; Martin J. Sullivan et al; *J. Clin Invest.*, vol. 76, Oct. 1985, 1632–1642.

Choo et al., Circ. Shock, 32/2, pp. 165–171 (1990).

Bendheim et al., Neurology, 35/5, pp. 746–749 (1985).

*Primary Examiner*—Phyllis G. Spivack
*Attorney, Agent, or Firm*—Hoffman, Wasson & Gitler, P.C.

[57] ABSTRACT

A method for maintaining strength during periods of inactivity, or enhancing strength, optionally in combination with exercise, through the use of beta-2 agonists which have been either orally ingested or inhaled.

8 Claims, 1 Drawing Sheet

BETA-AGONISTS AS AN AID TO MAINTAIN OR ENHANCE STRENGTH AND ENDURANCE

BACKGROUND OF THE INVENTION

This invention relates to the use of beta-agonists, namely a beta-2 agonist to enhance the effects of a strength training program or maintain endurance during periods of inactivity.

When combined with exercise training, the program results in increased power and endurance.

In the past, it has been contended that the intravenous use of dobutamine (a primary beta-1 agonist) has resulted in the maintenance of aerobic capacity in subjects placed at bedrest (see the Sullivan et al. publication entitled "Prevention of Bedrest-induced Physical Deconditioning by Daily Dobutamine Infusions".)

Inactivity or microgravity will result in muscle weakness and atrophy. During bedrest, muscle will loose 10–15% of strength per week and 50% in three to five weeks. Muscle bulk may be reduced by 50% in two months. Antigravity muscles such as quadriceps or gastrocnemius are affected the most.

Similar loss of strength is incurred during space flight. For example, measurements made before and after Skylab missions found a 25% decrease in gastrocnemius strength and decreased calf volume indicating muscle mass loss.

Decreases in maximal oxygen uptake and increased cardiovascular response to submaximal workloads occur quickly during bedrest. In some common bedrest studies of varying patients, there was found to be approximately a 9% decrease per week in aerobic capacity. Thus, the decrease in aerobic capacity with bedrest is significant. Investigations of the mechanisms have demonstrated that reduced plasma volume and cardiac stroke volume is the major mechanism. The reduction in aerobic capacity with inactivity can be effected by fitness level. Microgravity, especially when prolonged, has resulted in a similar reduction of aerobic capacity as bedrest.

Exercise has been utilized to prevent and reverse bedrest-induced changes in muscle strength and aerobic capacity. Isometric and isotonic exercise increase both strength and power.

Exercise programs have been utilized in U.S. and Russian space flights. Presently, space shuttle orbiter crew exercised for approximately one hour every other day and payload crew exercised every third day. In extended duration missions, the crews exercised two hours per day, increasing to about four hours per day, several weeks before returning to Earth. Resistance training in space such as on Skylab, has mitigated the loss of strength. Overall, exercise countermeasures have only been partially successful in preventing loss of strength, or loss of aerobic capacity.

An aerobic conditioning effect on Earth will depend on the intensity, frequency, and duration of exercise. It appears that as little as one to two workouts per week for 10–15 minutes at low workloads can achieve some conditioning effect but this will depend on the fitness level of the subject. For trained individuals, a threshold of intensity may be necessary. Intensity levels close to the anaerobic threshold appear most effective.

Beta-2 agonists exist in many forms and are used routinely for relief of bronchospasm in the treatment of airways disease such as asthma or chronic obstructive pulmonary disease. For example, isoproterenol is available in a sublingual form, a metered dose inhaler, and as solution. There are several beta-2 agonists such as albuterol that are available in tablet, solution, and metered dose inhaler form. The tablet forms of medication are safe, easy to use and do not require the level of monitoring that intravenous dobutamine or high dose nebulized solutions require.

It is an object of the present invention to devise a program for maintaining the strength and endurance for patient's subjected to bedrest for extended periods of time.

It is another object of the present invention to increase the strength, endurance and aerobic capacity of an individual alone or in combination with appropriate exercise.

SUMMARY OF THE INVENTION

The process of the present invention relates to the use of beta-2 agonists as an aid to maintain or enhance strength and endurance. The beta-2 agonists mitigates the loss of strength occurring from inactivity such as bedrest or zero gravity environments. Astronauts while on missions in space, where there is microgravity, undergo similar deconditioning and oral ingestion or inhalation, a beta-2 agonist is a useful countermeasure.

In has been found that the use of a beta-2 agonist, such as albuterol sulphate, enhances aerobic capacity and muscle strength.

DETAILED DESCRIPTION OF THE INVENTION

Figure 1:
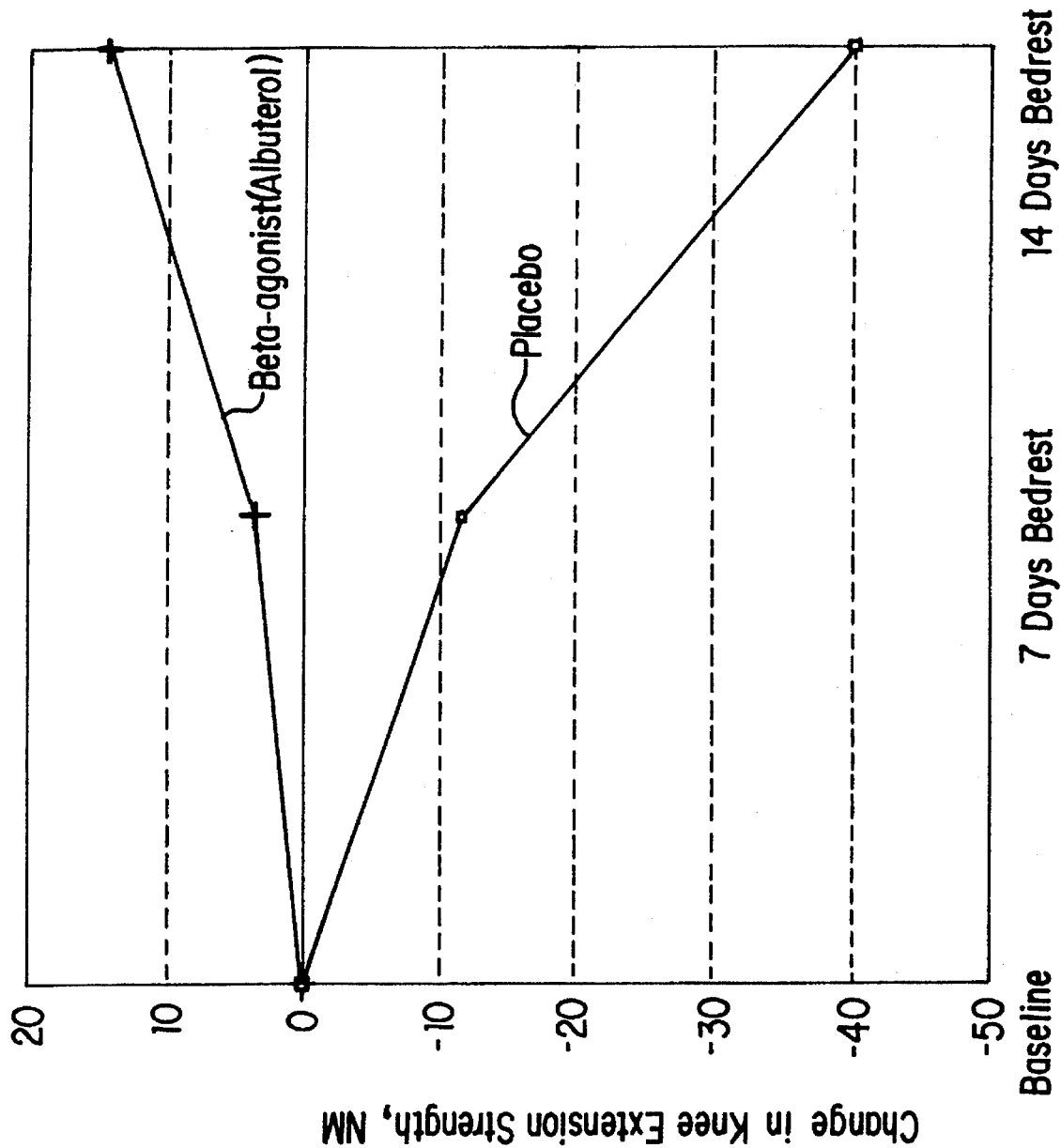
FIG. 1 is a graphic depiction of the change in strength verses bedrest of a patient performing the process of the present invention compared to a patient not undergoing the program.

Beta-2 agonists enhance the effects of a strength training program and endurance for individuals during a period of bedrest. There is disclosed a method or process for the use of beta agonists either alone or in combination with exercise, to maintain strength or aerobic capacity during periods of inactivity. The effects of one particular beta-2 agonist, albuterol sulphate, was tested. Two subjects were placed at bedrest for two 14 day trials each (see the graphical representation of FIG. 1). Maximum isometric strength was measured with an isotonic dynamometry machine before and after the trials. In one trial, the subjects received a placebo and in the other trial, the subjects received oral albuterol sulphate. The oral albuterol sulphate was administered at the rate of 24 mg per day in three divided doses. As demonstrated in the graphical representation as shown in FIG. 1, knee extension strength fell with the placebo but increased with the ingestion of oral albuterol sulphate.

Thus, a beta-2 agonist, such as oral albuterol, mitigates the loss of strength occurring from inactivity such as bedrest.

In addition, combining a beta-2 agonist such as albuterol sulphate with exercise enhances the effects of exercise. Furthermore, strength, endurance, and aerobic capacity can be benefitted by the use of a beta-2 agonist, such as albuterol sulphate alone or in combination with appropriate exercise. Similar beta-2 agonists such as terbutaline, isuprel, (isoproterenol), serevent or metaprel (metaproterenol) can also be used for enhancement. These drugs can be taken either in tablet or powder form, or inhaled, and similar benefits may be obtained.

The tablet forms of medication are safe, easy to use, and do not require the level of monitoring that intravenous solutions require.

Ingestion for benefit can be had through oral administration or inhalation of from 4 to 32 mg per day. A preferred range of from 16 to 24 mg per day will provide enhanced benefit. Three divided doses of the beta-2 agonist is also a preferred embodiment of the method.

While the invention has been described in terms of preferred embodiments, the claims appended hereto are intended to encompass all embodiments which fall within the spirit of the invention.

What is claimed is:

1. A method of maintaining human muscle strength during inactivity or enhancing human muscle strength and endurance comprising the oral ingestion or inhalation of a beta-2 agonist.

2. A method of maintaining human muscle strength during inactivity or enhancing human muscle strength and endurance in accordance with claim 1 further comprising the step of exercise.

3. A method of maintaining human muscle strength during inactivity or enhancing human muscle strength and endurance in accordance with claim 1 wherein said beta-2 agonist is selected from the group consisting of albuterol sulphate, terbutaline, isoproterenol, solmeterol and metaproterenol.

4. A method of maintaining human muscle strength during inactivity or enhancing human muscle strength and endurance in accordance with claim 1 wherein said beta-2 agonist is ingested at the rate of from 4 to 32 mg per day.

5. A method of maintaining human muscle strength during inactivity or enhancing human muscle strength and endurance in accordance with claim 1 wherein said beta-2 agonist is ingested at the rate of from 16 to 24 mg per day.

6. A method of maintaining human muscle strength during inactivity or enhancing human muscle strength and endurance in accordance with claim 1 wherein said beta-2 agonist is orally ingested or inhaled in three divided doses per day.

7. A method of maintaining human muscle strength during inactivity or enhancing human muscle strength and endurance comprising the oral ingestion or inhalation of albuterol wherein said albuterol is orally ingested or inhaled from 4 to 32 mg per day.

8. A method of maintaining human muscle strength during inactivity or enhancing human muscle strength and endurance comprising the oral ingestion or inhalation in accordance with claim 7 wherein said albuterol is orally ingested or inhaled in three divided doses per day.

* * * * *